(12) United States Patent
Smith

(10) Patent No.: US 6,632,195 B1
(45) Date of Patent: Oct. 14, 2003

(54) VERSATILE ADJUSTABLE LIQUID APPLICATOR

(76) Inventor: Karl R. Smith, Suite 5K, 1620 S. Ocean Blvd., Pompano Beach, FL (US) 33062

( * ) Notice: Subject to any disclaimer, the term of this patent is extended or adjusted under 35 U.S.C. 154(b) by 0 days.

(21) Appl. No.: 10/051,547

(22) Filed: Jan. 22, 2002

(51) Int. Cl.[7] .................. A61M 5/178; A61M 31/00; A61M 35/00
(52) U.S. Cl. ............... 604/36; 604/514; 604/517; 604/275; 604/310
(58) Field of Search ................. 604/36, 37, 41, 604/42, 48, 514, 517, 73, 181, 185, 212, 213, 264, 275–279, 911, 289–290, 310; 4/615–618; 239/390–397, 587.5, 587.6; 137/615; 222/526–527, 533

(56) References Cited

U.S. PATENT DOCUMENTS

| 3,310,813 | A | | 3/1967 | Jonsson |
| 3,680,780 | A | * | 8/1972 | Arbon ..................... 239/26 |
| 5,274,856 | A | | 1/1994 | Bernard |
| 5,667,146 | A | * | 9/1997 | Pimentel et al. ......... 239/587.1 |
| 5,889,275 | A | * | 3/1999 | Chen ..................... 239/391 |
| 5,946,741 | A | | 9/1999 | Moon |
| 5,947,388 | A | * | 9/1999 | Woodruff ................. 239/532 |
| 6,026,535 | A | * | 2/2000 | Lankowski .............. 15/209.1 |
| 6,110,150 | A | | 8/2000 | Singo |
| 2002/0040500 | A1 | * | 4/2002 | Noguchi et al. ............ 4/596 |

* cited by examiner

Primary Examiner—Brian L. Casler
Assistant Examiner—Catherine Serke
(74) Attorney, Agent, or Firm—Alvin S. Blum

(57) ABSTRACT

An applicator for applying fluid from a squeeze bottle to various parts of the body that may be difficult to reach includes two rigid arms connected by an adjustable angle joint. One end of the first arm screws onto the bottle. The other end of the second arm ends in a tubular connector such as a grease gun fitting. A flexible tube provides a fluid passage between the bottle and the tubular connector. A variety of terminals for different purposes can sealingly snap onto the tubular connector. The terminals preferably have a grease fitting for easy connection. The terminals may include an enema tip, a douche tip, a bidet tip and a suntan lotion spreader. The arms may retract telescopically for compact transport and storage.

6 Claims, 3 Drawing Sheets

VERSATILE ADJUSTABLE LIQUID APPLICATOR

This invention relates to liquid applicators, and more particularly to an adjustable device that can apply liquid to portions of the body that are not readily accessible to the user, for dispensing suntan lotion or enemas, for example.

BACKGROUND OF THE INVENTION

Because of disabilities, some individuals may not be able to perform certain tasks. In other circumstances, asking for help may be embarrassing. Some of these tasks include the application of fluids to the body, such as or enema fluids or douches or suntan lotion to the back,. It is even more awkward when the tasks must be performed away from home.

SUMMARY OF THE INVENTION

It is accordingly an object of the invention to provide a portable device that may be used to apply a variety of fluids to various parts of the body without assistance from another party. It is another object that the device shall be operable with fluids that are in their original flexible plastic bottles. It is yet another object that the device shall be adjustable to apply fluid to various body areas that are difficult to reach.

These and other objects, features, and advantages of the invention will become more apparent when the detailed description is studied in conjunction with the drawings in which like elements are designated by like reference characters in the various drawing figures.

DETAILED DESCRIPTION OF PREFERRED EMBODIMENTS

Figure 3:
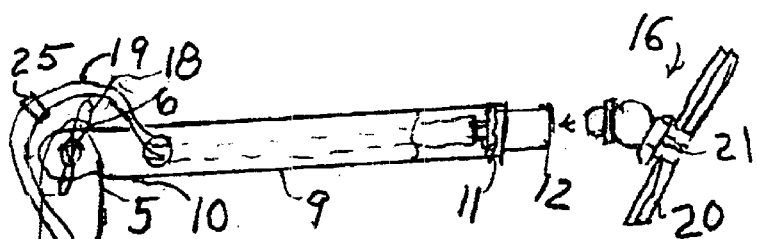
FIG. 3 is a perspective view of an applicator partially broken away.
Figure 3:
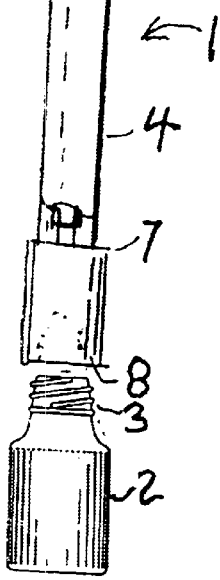

Referring now first to FIGS. 1–4, the versatile adjustable applicator 1 of the invention is designed to receive a flexible squeeze bottle 2 containing the fluid to be applied and having a standard male thread 3. That is screwed into a female threaded tubular connector 8 affixed to a second end 7 of first elongate rigid arm 4. A first end 5 of arm 4 terminates in a pivot joint 6 connected to a first end 10 of second elongate rigid arm 9 that may be fixed at any selected angle by wing nut 18. A second end 11 of arm 9 terminates in a tubular coupling 12. An elongate flexible tube 19 provides a fluid communication between the tubular coupling 12 and the tubular connector 8. A valve 25 may optionally be provided, although the squeeze bottle gives good control for many applications. The tubular coupling 12 is preferably a grease gun fitting adapted for sealingly connecting with grease fittings. The various interchangeable terminals that may be used with this invention are each provided with a fitting that sealingly connects with coupling 12. These are preferably the grease fittings that may be provided with a straight through passage, or 90 degrees, or 135 degrees. These fitting have distinct advantages in this application. They simply snap in to provide a fluid tight joint, yet they provide a freedom of movement through a considerable angle. The fittings are readily available at low cost. The enema terminal 13 has a 90 degree angle. A pull knob 17 may facilitate insertion. A suntan lotion applicator 16 feeds lotion through a center hole 21 and an annular sponge pad 20 helps spread the lotion over body areas not readily accessible. A douche tip terminal 22 may also be provided.

Figure 5:
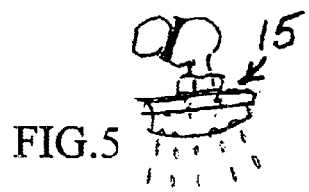
FIG. 5 is a front elevation view of a bidet terminal for the applicator.
Figure 1:
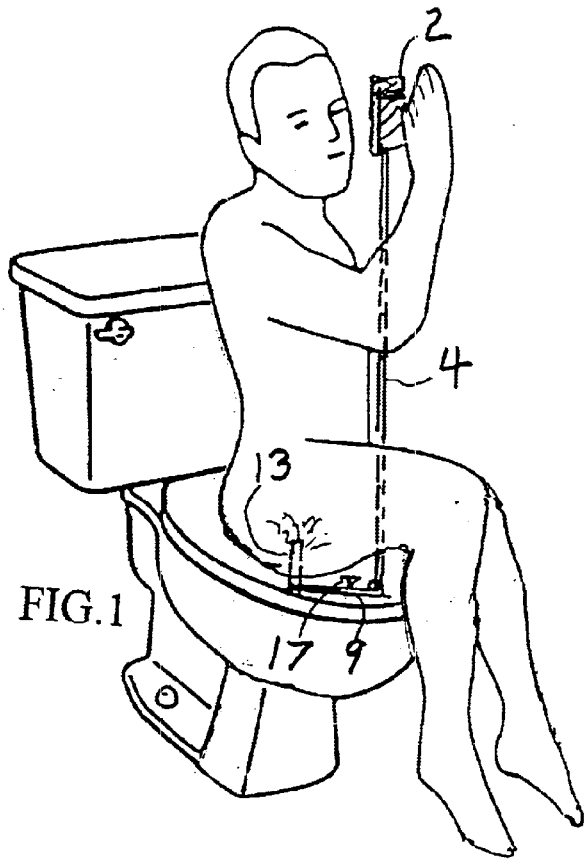
FIG. 1 is a perspective drawing of a device of the invention in use for administering an enema.
Figure 2:
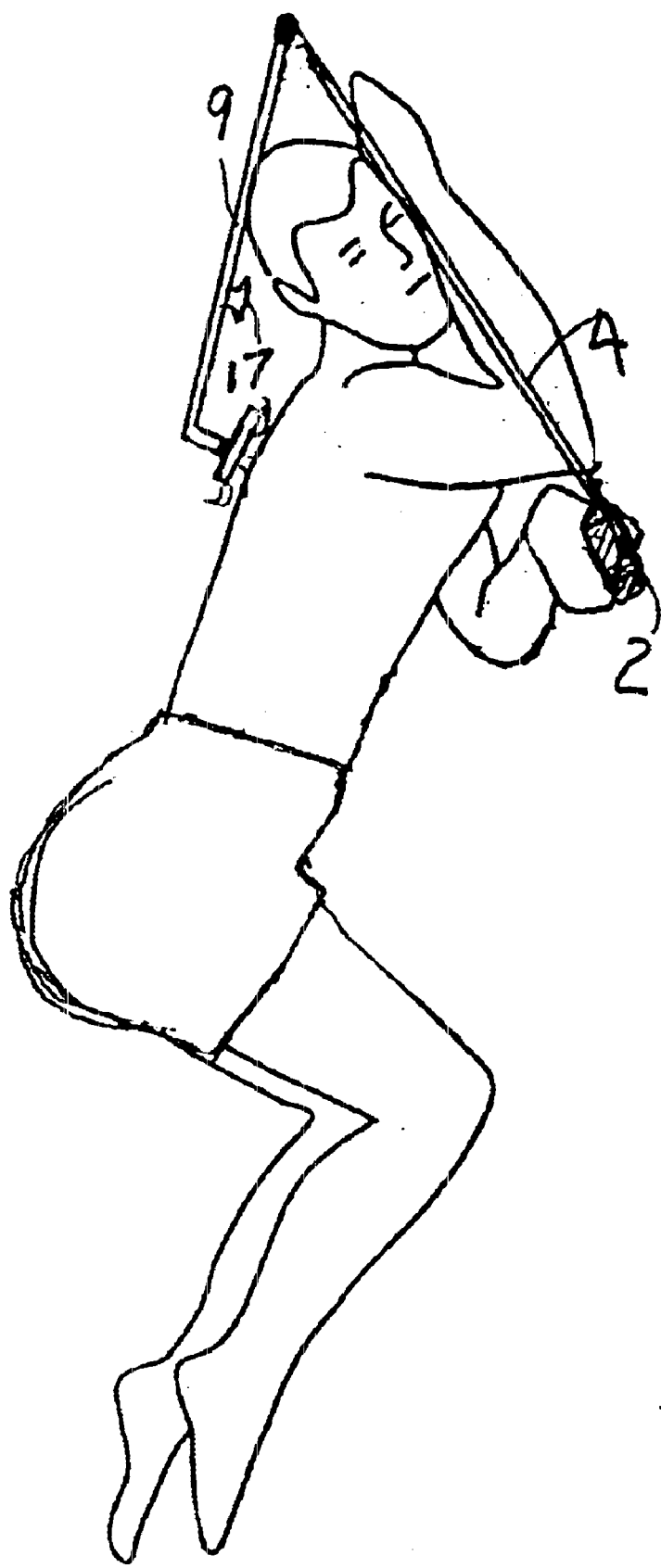
FIG. 2 is a perspective view of a device of the invention in use for applying suntan lotion.

A bidet terminal 15 shown in FIG. 5 had a 135 degree angle and provides a spray.

Figure 4:
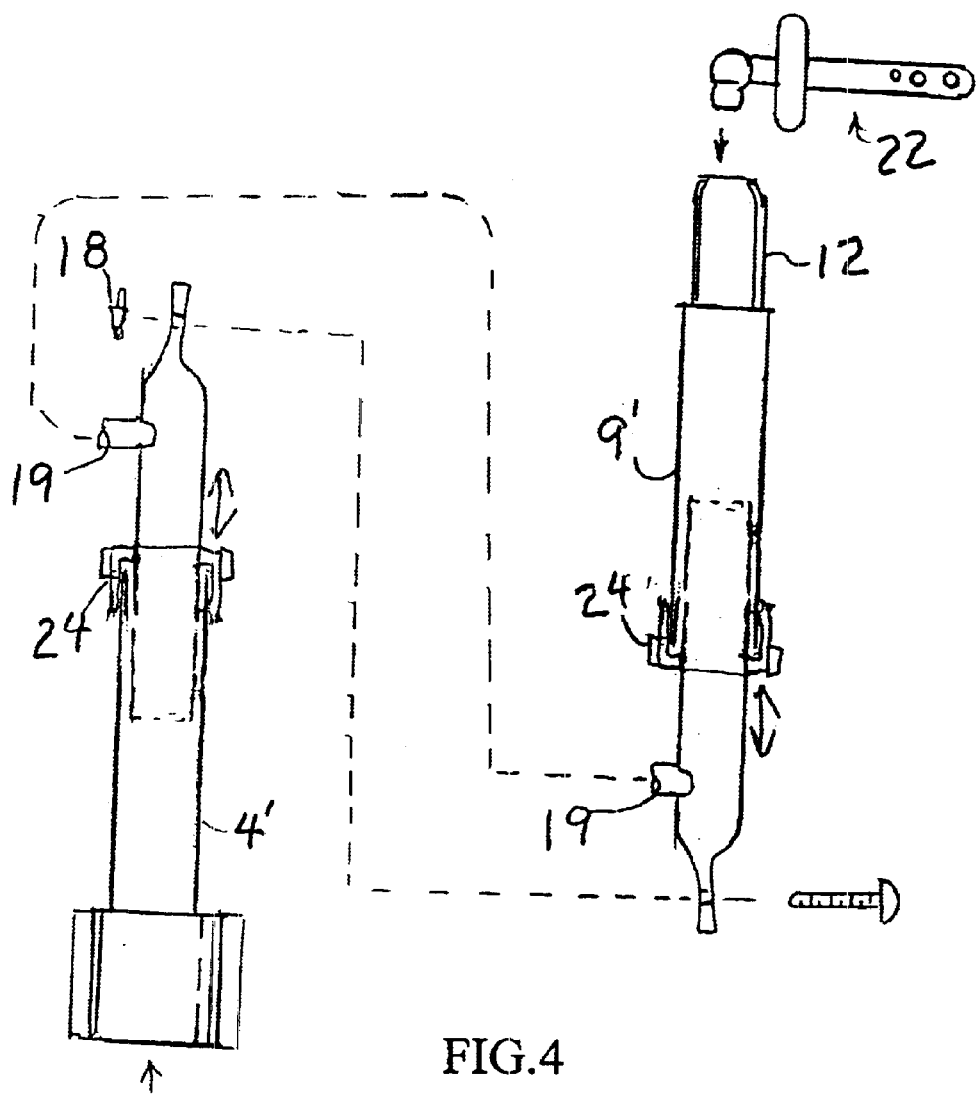
FIG. 4 is an exploded view of another embodiment of the applicator.

As best seen in FIG. 4, the rigid arms 4' and 9' may be telescopically adjustable in length by adjustments 24. This is most convenient when the user must travel away from home, but needs the apparatus. By reducing the arm length, the device may be folded into a small inconspicuous carrying case.

An empty bottle 2 may be provided that is to be filled with fluid by the user.

While I have shown and described the preferred embodiments of my invention, it will be understood that the invention may be embodied otherwise than as herein specifically illustrated or described, and that certain changes in form and arrangement of parts and the specific manner of practicing the invention may be made within the underlying idea or principles of the invention.

What is claimed is:

1. An applicator for applying fluids to various body portions from a squeeze bottle that has a male thread for a closure, the applicator comprising:
    a) a first elongate rigid arm;
    b) a second elongate rigid arm joined at a first end to a first end of the first arm by a pivot joint that may be adjustably fixed at a selected angle;
    c) a variety of fluid dispensing terminals for selected body application purposes, the terminals selected from the group of terminals consisting of enema tip; body lotion dispenser with pad; bidet tip; and douche tip;
    d) a tubular coupling affixed at a second end of the second arm, the coupling adapted for sealingly coupling interchangeably to the variety of fluid dispensing terminals for selected body application purposes;
    e) a threaded tubular connector affixed at a second end of the first arm with a female thread corresponding to the male thread of the squeeze bottle for sealing connection thereto; and
    f) an elongate tubular fluid passage in fluid communication with the tubular coupling and the threaded tubular connector for passage of fluid therebetween.

2. The applicator according to claim 1, in which the tubular coupling emulates a grease gun fitting, and each of the dispensing terminals is provided with a connector that emulates a grease fitting.

3. The applicator according to claim 2, in which the first and second elongate rigid arms may be telescopically adjusted for length.

4. The applicator according to claim 1, in which the first and second elongate rigid arms may be telescopically adjusted for length.

5. The applicator according to claim 1, in which the tubular fluid passage is a flexible tube.

6. The applicator according to claim 1, further comprising a valve in the tubular fluid passage.

\* \* \* \* \*